United States Patent
Hoyoux et al.

(10) Patent No.: US 6,727,084 B1
(45) Date of Patent: Apr. 27, 2004

(54) COLD-ACTIVE BETA-GALACTOSIDASE, THE PROCESS FOR ITS PREPARATION AND THE USE THEREOF

(75) Inventors: Anne Hoyoux, Tilff (BE); Jean-Marie François, Soheit-Tinlot (BE); Phillip Dubois, Liege (BE); Etienne Baise, Binche (BE); Isabell Jennes, Charneux (BE); Sabine Genicot, Roscoff (FR); Charles Gerday, Esneux (BE)

(73) Assignee: Universite de Liege, Liege (BE)

( * ) Notice: Subject to any disclaimer, the term of this patent is extended or adjusted under 35 U.S.C. 154(b) by 0 days.

(21) Appl. No.: 09/501,136

(22) Filed: Feb. 9, 2000

Related U.S. Application Data
(60) Provisional application No. 60/143,114, filed on Jul. 9, 1999.

(30) Foreign Application Priority Data

Nov. 24, 1999 (BE) ........................................ BE99/00152

(51) Int. Cl.$^7$ .......................... C12N 9/38; C07H 21/04; C07K 1/00
(52) U.S. Cl. ........................ 435/207; 435/183; 435/267; 435/252.3; 435/320.1; 530/350; 536/23.1; 536/23.2; 536/23.7
(58) Field of Search ................................ 435/183, 207, 435/267, 252.3, 320.1; 530/350; 536/23.1, 23.2, 23.7

(56) References Cited

U.S. PATENT DOCUMENTS

| | | | |
|---|---|---|---|
| 4,007,283 A | 2/1977 | Crisan et al. | 426/34 |
| 4,237,230 A | 12/1980 | Iida et al. | 435/207 |

FOREIGN PATENT DOCUMENTS

| | | |
|---|---|---|
| WO | WO 92/02143 | 2/1992 |
| WO | WO 01/04276 A1 * | 1/2001 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Hoyoux et al. Cold–adapted b–galactosidase from Antartic Psychrophile Pseudoaltermonas haloplanktis, Applied and Environmental Microbiology, vol. 67, No. 4, Apr. 2001, pp. 1529–1535.*
Hoyoux et al., "A Cold Adapted β–Galactosidase from Antarctic Bacteria", Laboratory of Biochemistry, Institute of Chemistry B6, University of Liege, B–4000 Liege, Bioforum, May 1999.
JM Francois et al., "A Cold Adapted Bacterial β–Galactosidase from Antarctica", Database EMBL On–Line, (1998). Accession No. AJ131635.
Richard Y. Morita, "Psychrophilic Bacteria", Bacteriological Reviews, vol. 39, No. 2, pp. 144–167 (1975).
Godfrey et al., "The Application of Enzymes in Industry", Industrial Enzymology, The Nature Press, Chapter 4 pp. 268–277 (1983).
Donald E. Trimbur et al., "Characterization of a Psychrotrophic Arthrobacter Gene and its Cold–Active β–Galactosidase", Applied and Environmental Microbiology, vol. 60, pp. 4544–1552 (1994).
Khalid A.A. Rahim et al., "Production and Characterization of β–Galactosidase from Psychrotrophic Bacillus Subtilis KL88", Biotechnology and Applied Biochemistry, vol. 13, pp. 246–256 (1991).

* cited by examiner

*Primary Examiner*—Richard Hutson
(74) *Attorney, Agent, or Firm*—Venable LLP; Robert Kinberg; Nancy J. Axelrod

(57) ABSTRACT

A purified cold-active beta galactosidase enzyme, specific for lactose, having a stable enzymatic activity at a temperature below 8° C. In the presence of lactose, a purified cold-active beta galactosidase enzyme, specific for lactose, having a stable enzymatic activity at a temperature ranging between 0° C. and 50° C.

24 Claims, 4 Drawing Sheets

COLD-ACTIVE BETA-GALACTOSIDASE, THE PROCESS FOR ITS PREPARATION AND THE USE THEREOF

CROSS-REFERENCE TO RELATED APPLICATION

The present application claims the priority of U.S. Provisional Application 60/143,114 filed Jul. 9, 1999 which is hereby incorporated by reference in its entirety.

FIELD OF THE INVENTION

The present invention relates to a purified β-galactosidase specific for lactose.

β-galactosidase catalyzes the hydrolysis of lactose disaccharide into its constituent monosaccharides, glucose and galactose.

DESCRIPTION OF THE RELATED ART

This enzyme is widely distributed in numerous microorganisms, plant and animal tissues.

The ability of β-galactosidase to hydrolyse lactose into galactose is applied in food industry, particularly in the field of dairy products because of the nutritional (lactose intolerance), technological (crystallisation) and environmental (pollution) problems associated with lactose (Triveni P. S., 1975, CRC Critical Reviews in Food Technology 325–354). The added value gained by the hydrolysis of lactose, to its constituent monosaccharides glucose and galactose, lies in the increased usefulness of hydrolysed lactose as a food carbohydrate. Lactose itself has limited use in this respect because of its relatively low sweetness, solubility and digestibility, but the hydrolysis products of lactose, i.e. glucose and galactose, are superior in all of these respects. Increased sweetness and solubility improve the technical usefulness of whey products while the increased digestibility of hydrolysed lactose also offers the opportunity of supplying milk solids to populations which have hitherto been unable to consume milk products because of their inability to hydrolyse lactose in the digestive tract.

The β-galactosidase can be applied to the production of low-lactose milk and in the production of galactose or glucose from lactose contained in milk serum which is formed in large amount in the process of producing cheese.

The major applications for lactose hydrolysis are listed below.

a) Liquid milk. Lactose hydrolysis in liquid milk improves digestibility for lactose intolerant consumers. In flavoured milks, lactose hydrolysis increases sweetness and enhances flavours.

b) Milk powders. Lactose hydrolysed milk powders for dietetic uses, especially for infants with temporary β-galactosidase deficiency.

c) Fermented milk products. In some cases, lactose hydrolysis in milk used for the manufacture of cheese and yoghurt can increase the rate of acid development and thus reduce processing time.

d) Concentrated milk products. Lactose hydrolysis in concentrated milk products (e.g. sweetened condensed milk, ice cream) prevents crystallisation of lactose.

e) Whey for animal feed. Lactose hydrolysis in whey enables more whey solids to be fed to pigs and cattle and also prevents crystallisation in whey concentrate.

f) Whey. Lactose hydrolysed whey is concentrated to produce a syrup containing 70–75 per cent solids. This syrup provides a source of functional whey protein and sweet carbohydrate and is used as a food ingredient in ice cream, bakery and confectionery products.

The conventional approach in food processing is to carry out the hydrolysis of lactose at 40° C. during approximately four hours. (T. Godfrey and J. Reichelt in : "Industrial Enzymology: the application of enzymes in industry"; The Nature Press, Mac Millan Publishers Ltd, GB, 1983). However, milk or lactose solution as a raw material is a preferable nutrition source for bacteria. As the result, the putrefaction owing to the saprophyte contamination during the treatment is a serious problem in the food production. Thus, the fact is that the conventional β-galactosidase is not put into practical use.

Attempts to solve these problems consisted in using thermophilic enzymes as described in U.S. Pat. No. 4,237,230 and U.S. Pat. No. 4,007,283 but a problem of high energetic cost still remains.

On another hand, cold-adapted β-galactosidases have been studied (Trimbur D. E. and al., 1994, Appl. Environ. Microbiol. 60:4544–4552; Rahim K. A. A. and Leb B. H., 1991, Biotechnol and Appl. Biochem., 13, 246–256).

However, these β-galactosidases generally known in the prior art, when used for food processing, all have one or more disadvantages such as low enzyme activity and low stability at a temperature below 20° C., narrow range of optimum pH and the inhibition of enzymatic action by a reaction product, such galactose or others products particularly calcium.

SUMMARY OF THE INVENTION

The object of the present invention is to hydrolyse lactose by using a β-galactosidase, which could overcome the above-mentioned drawbacks which are usually associated to this process, while advantageously avoiding contamination problems during the hydrolysis process and lowering the energy consumption.

This problem is solved according to the present invention by a purified cold-active β-galactosidase, specific for lactose, having a stable enzymatic activity at temperatures up to below 8° C., preferably up to below 6° C., and specifically at 4° C., which corresponds to refrigerating conservation temperature for dairy products. This enzyme of the invention is consequently able to hydrolyse lactose in dairy products and stable enzymatic activity at temperatures up to below 8° C., preferably up to below 6° C., and specifically at 4° C., which corresponds to refrigerating conservation temperature for dairy products. This enzyme of the invention is consequently able to hydrolyse lactose in dairy products and milk processing at such a low temperature that saprophytes are hindered to proliferate. The hydrolysis of lactose can be carried out in these refrigeration conditions with no need of a particular treatment to the dairy product concerned.

According to the invention, an enzymatic activity is considered as stable when, in the concerned conditions, the enzyme is capable of lasting long enough to obtain the desired effect, for example, the hydrolysis of a substrate.

According to an embodiment of the invention, the cold-active β-galactosidase has a stable enzymatic activity between 0 and 50° C.

Advantageously, the cold-active β-galactosidase according to the invention has a stable enzymatic activity at a pH range from 6 to 10, preferably from 6 to 8.

Preferably, the cold-active β-galactosidase according to the invention has a stable enzymatic activity in presence of calcium and/or galactose, meaning that the activity of this enzyme is neither inhibited by its reaction product nor by products being present in milk. This property allows to use efficiently this enzyme in milk treatment.

Such a cold-adapted β-galactosidase according to the invention attains the level of practical application, having simultaneously the following properties:

(1) Having a sufficient stability in the neighbourhood of 0 to 10° C.
(2) Having a sufficient enzymatic activity at a pH range from 6 to 10
(3) Having an enzymatic activity non inhibited by reaction products or other products substantially present in milk, such calcium.

According to an advantageous embodiment of the invention, the enzyme can be inactivated at a pasteurisation temperature. This property of the enzyme according to the present invention allows to apply the β-galactosidase according to the invention and to stop the enzymatic reaction of lactose hydrolysis without any additional step during a current milk treatment.

Another object of the present invention is a strain of an isolated psychrophilic bacterium capable of producing a cold-active β-galactosidase according to the present invention. A preferable strain is *Pseudoalteromonas haloplanktis* deposited on the Nov. 4, 1999, under the Budapest Treaty at the Belgian Coordinated Collections of Microorganisms (BCCM™), Laboratorium voor Microbiologie—Bacteriënverzameling (BCCM™/LMG), Universiteit Gent, K. L. Ledeganckstraat 35, 9000 Gent, Belgium, with the Accession NO LMG P-19143 and variants and mutants derived therefrom.

To purify a cold-active β-galactosidase according to the invention, a bacterium living in the Antarctic area was isolated and characterised in order to study how its enzymes, and particularly, the β-galactosidase was adapted to cold. These studies led to the purification of the β-galactosidase, meaning that this protein was obtained substantially free of other proteins as determined by Sodium Dodecyl Sulphate Polyacrylamide gel Electrophoresis (SDS-PAGE) using protein purification steps known in the art.

Micro-organisms can be divided in categories depending on the temperature at which they can proliferate. The widely accepted definition by Morita (Psychrophilic bacteria. Bacteriol. Rev. 39: 144–167; 1975.) proposes that psychrophiles include organisms having optimum growth temperatures <15° C. and upper cardinal temperatures around 20° C., although they are able to multiply and to carry out all their biochemical functions near the normal freezing point of water. The mesophilic bacteria proliferate at an average temperature range between 25 and around 40° C. Thermophilic micro-organisms proliferate at a temperature above 50° C. and hyperthermophilic micro-organisms grow at temperatures above 80° C.

As a general rule, micro-organisms which are pathogenic for human and animals are mesophilic, so it is interesting to carry out industrial food processing at low temperatures to avoid the possible proliferation of such pathogens.

It is still an object of the present invention to provide a DNA sequence comprising a gene which encodes a polypeptide having the biological activity of the cold-active β-galactosidase according to the invention. A preferable DNA sequence is shown in SEQ ID NO: 1 and a polypeptide having an amino acid sequence as shown in SEQ ID NO: 2 is preferable.

Another object of the invention is a recombinant plasmid suited for transformation of a host, capable of directing the expression of a DNA sequence according to the invention in such a manner that the host expresses said polypeptide having the biological activity of the cold-active β-galactosidase in recoverable form. According to the invention another object is the so transformed host.

A variety of host-expression systems may be conceived to express the cold-active β-galactosidase coding sequence, for example bacteria, yeast, insect cells, plant cells, mammalian cells, etc.

Particularly, in yeast, a number of vectors containing constitutive or inducible promoters may be used. For a review see Grant and al., 1987, Expression and secretion vectors for yeast, in Methods in Enzymology, Eds. Wu & Grossman, 31987, Acad. Press, N.Y., Vol. 153, pp. 516–544.

It is also an object of the present invention to provide a process for purifying the cold-active β-galactosidase according to the invention from a psychrophilic bacterium as well as to provide a process for producing cold-active β-galactosidase according to the invention in a transformed host.

These and other objects of the present invention will be apparent from the following disclosure.

Other characteristics of the present invention are listed in the annexed claims.

DESCRIPTION OF THE PREFERRED EMBODIMENTS

Figure 1A:
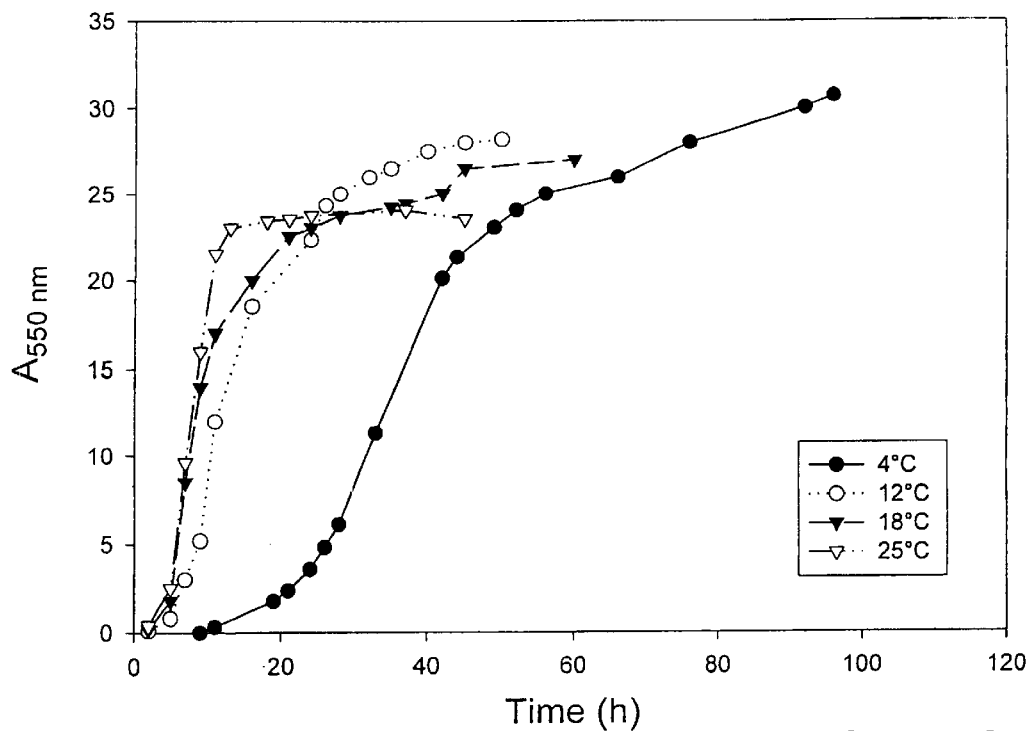
FIG. 1a shows the growth of the strain *Pseudoalteromonas haloplanktis* LMG P-19143 at different temperatures.

Screening of a Bacterial Strain and Culture Conditions

A bacterial strain was isolated and selected from sea water on necrosed algae at the J. S. Dumont d'Urville Antarctic Station (60°40'S; 40°01'E) The strain was identified as a *Pseudoalteromonas haloplanktis* by identification systems such the quantitative analysis of cellular fatty acid composition performed using a gas-liquid chromatography procedure known in the Art (Mergaert et al, 1993, Int. J. Syst. Bacteriol., 43, 162–173), using the Microbial Identification System (MIS, Microbial ID Inc., Newark, Del., U.S.A.). The peak recognition program was the MIS TSBA40 database for fatty acids and the chromatographic profiles were identified by comparison to the MIS TSBA database for aerobic bacteria (version 4.0).

The identified strain was then deposited according to the Budapest Treaty at the BCCM™ (Belgian Coordinated Collections of Microorganisms) with the following Accession Number: LMG P-19143, on the Nov. 4, 1999.

The screening of strains collected in the Antarctic, for showing a β-galactosidase activity, was carried out on L-agar plates containing 10 g/l bactotryptone, 5 g/l yeast extract, 25 g/l sea salts, 17 g/l agar (Difco) with 0,2% lactose, 32 mg/l X-Gal (5-Bromo4-chloro-3-indolyl-β-D-galactopyranoside) (Eurogentec) with or without 1 mM IPTG (isopropyl-thio-β-D-galactopyranoside) (Sigma); Growth properties were studied in L-Broth (10 g tryptone, 5 g yeast extract, 30 g sea salts in 1L at pH8,5) containing 1% or 2% lactose. Cultures inoculated with 10 ml of a pre-culture grown at 4° C. were run at 250 rpm in 500 ml Erlenmeyer flasks containing 300 ml culture medium. After 115 hours culture, the absorbance of the culture was measured at 550 nm and the cells were pelleted and sonicated.

The definition of enzyme activity units can be defined according to the substrate used with lactose as a substrate, the unit of activity is defined as the amount of enzyme which releases one micro-mole glucose in one minute under standard reaction conditions (temperature, pH). Another commonly used substrate is ortho-nitrophenyl-β-D galactopyranoside (ONPG) and in this case, the unit of activity is defined as the amount of enzyme which hydrolyses one micro-mole of ONPG in one minute under standard reaction conditions.

The degree of hydrolysis, defined as the percentage of lactose molecules cleaved, is most simply measured by determination of the amount of glucose released, or by changes in the physical properties of the hydrolysed lactose solution. Solution properties such as freezing point depression change as the disaccharide lactose is converted into the lower molecular weight monosaccharides glucose and galactose.

The intracellular β-galactosidase activity was assayed using ONPG as substrate. When 1 mM IPTG was added to the culture, the β-galactosidase activity was enhanced at least 2 times in the strain selected among the bacterial samples collected. This selected strain was a Gram negative and protease positive bacterium, chosen for its high β-galactosidase activity and its growth properties in liquid medium.

The strain was characterised and different growth conditions were tested. Sea salts at different concentrations were added to the culture medium: 5, 10, and 30 g/l with a lactose concentration of 10 or 20 g/l. The optimum growth medium was a rich medium comprising 2% lactose and 3% sea salts. In particular, the addition of sea salts to the growth medium enhanced the growth of the strain by a factor of ten.

The effects of adding IPTG in the growth medium were also studied and three IPTG concentrations were tested: 0.1 mM, 1 mM and 10 mM. It was observed that the addition of 1 mM IPTG to the growth medium after 44 hours of culture doubles the β-galactosidase activity in the cells.

Figure 1B:
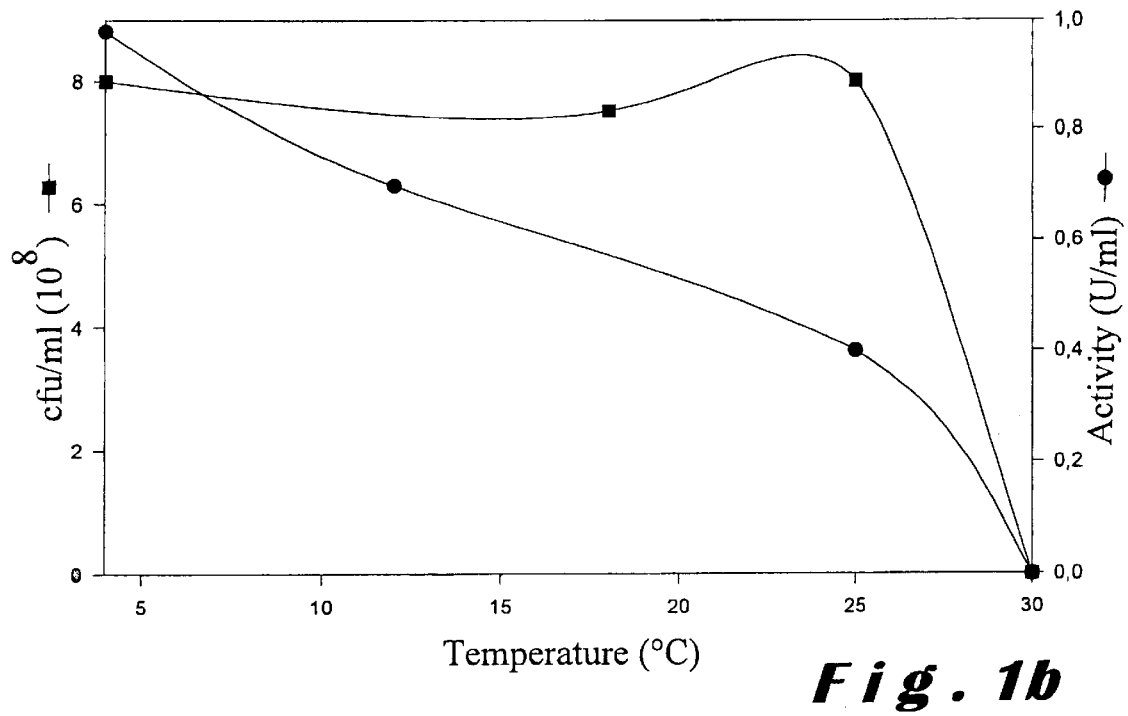
FIG. 1b shows the cell viability and the cold-active β-galactosidase activity of the strain *Pseudoalteromonas haloplanktis* LMG P-19143 versus temperatures.

FIG. 1a shows the growth rates of the strain at four temperatures: 4° C., 12° C., 18° C. and 25° C. by measuring the absorbance of the culture at 550 nm. The results obtained showed that temperatures above 4° C. induced faster growth rates but in the same time, reduced strain development. It is worth mentioning that growth rates are inaccurate as a sole criterion to determine the optimal growth temperature. This is clearly illustrated by the FIG. 1b showing the cell viability and the β-galactosidase activity of the strain of the invention at different temperatures.

The β-galactosidase from *Escherichia coli* used as a control was from Sigma (G2513).

The assay of β-galactosidase was carried out using 3 mM ONPG (ortho-nitrophenyl-β-galactopyranoside) as a chromogenic substrate in 100 mM sodium phosphate buffer, pH 7,3, 1 mM $MgCl_2$, 100 mM 2-mercaptoethanol (Sigma). Activities toward the chromogenic substrate were recorded in a thermostated Uvicon 860 Spectrophotometer (Kontron) at 25° C. and calculated on the basis of an extinction coefficient for o-nitrophenol of 3.5 $mM^{-1}$ $cm^{-1}$ at 410 nm (Miller, J. H. and Reznikoff, W. S., Eds. 1978; The Operon. Cold Spring Harbor Laboratory Press, N.Y.). Assays using lactose as a substrate were carried out using various concentrations of lactose. The reaction was stopped by boiling the sample in a water bath for 3 minutes. The galactose dehydrogenase assay was used to measure the amount of galactose released by the enzyme (Schachter H. 1975, Enzymatic microassays for D-Mannose, D-Glucose, D-Galactose, L-Fucose, and D-Glucosamine. Methods Enzymol., 41: 3–10.) The specific activity of β-galactosidase is defined as micro-moles of galactose released per minute per mg of protein.

Purification and Characterization of a Cold-active β-galactosidase From the Strain LMG P-19143 of the Present Invention The Antarctic strain was cultivated at 4° C. for 5 days in ten litres of LB broth containing 2% lactose. After 44 hours, the culture was induced by ITPG (isopropyl-L-thio-β-D-galactopyranoside) to a final concentration of 1 mM and left for 68 hours.

The cells were harvested by centrifugation at 12,000×g for 60 minutes at 4° C. and re-suspended in 200 ml 50 mM MOPS (3-morpholinopropanesulfonic acid) buffer, pH 7,5. The cell-free extract was prepared by cell desintegration using the disruptor (LH-SGI Inceltech). 1 mM PMSF (Phenyl-methyl-sulphonyl-fluoride) was added to the crude extract to neutralise serine active proteases and debris were removed by centrifugation at 15,000×g for 30 minutes. Supernatant was then treated for two hours by protamine sulphate at a final concentration of 1 g/l to remove nucleic acids. After centrifugation for 30 minutes at 27000×g, the supernatant wad dialysed against 2×2 litres of MOPS buffer and then loaded on a DEAE-agarose column (35×2.5 cm) equilibrated in MOPS buffer and eluted with a NaCl linear gradient (500 ml–500 ml, 1M, NaCl). Fractions containing β-galactosidase activity were pooled, concentrated up to 20 ml and dia-filtrated againts MOPS buffer using a Minitan tangential flow ultra-filtration unit (Millipore) fitted with PTHK membrane (100 kDa molecular mass limit). The sample was then added to an affinity matrix of agarose derivatized with p-aminobenzyl-1-thio-β-D-galactopyranoside (Sigma A0414) (Steers E., Jr., Cuatrecasas P., and Pollard H., B., 1971, J. Biol. Chem. 246:196–200). The matrix containing the sample was washed with 1M KCl and eluted with 100 mM lactose in MOPS buffer containing 1M KCl. The active fractions were pooled and applied on a Sephacryl S-300 column (95×3 cm) eluted with MOPS buffer.

Several steps were necessary to purify to homogeneity β-galactosidase from LMG P-19143. These steps are summarised in Table 1.

TABLE I

Purification of the intracellular β-galactosidase from LMG P-19143
One unit of β-galactosidase is defined as the amount of the enzyme required to release 1 μmole of nitrophenol min at pH 7.3 and at 20° C.

| Purification step | Vol (ml) | Protein (mg) | Total activity (μmol/min) | Sp act (μmol/min/mg) | Recovery (%) | Purification (fold) |
|---|---|---|---|---|---|---|
| Crude extract | 200 | 1480 | 6954 | 4.7 | 100 | 1 |
| DEAE-agarose | 80 | 178.4 | 3101 | 1704 | 45 | 3.7 |
| Affinity Chromatography | 6 | 9.1 | 2509 | 276.5 | 36 | 58.8 |

Upon loading on DEAE sepharose column, β-galactosidase was eluted as a single peak at a NaCl concentration of approximately 400 nM. Although the affinity column decreased the yield of active β-galactosidase, it increased the purity by removing other remaining contaminant proteins. From 2L culture grown under the conditions described above, the yield of purified β-galactosidase amounted to 10 ng. Following this procedure, the enzyme is 99% pure as determined by SDS-PAGE and has an estimated apparent molecular mass of 118 kDa. Ultrafiltration tests showed that β-galactosidase from LMG P-19143 is concentrated by an ultra-filtration membrane displaying a cut off of 300 kDa.

Analytical Procedures

Protein concentrations were determined by the method of Bradford (Bradford, M. M., 1976, Anal. Biochem. 72:248–254) using reagents from Pierce and bovine serum albumin as standard. For the purified enzyme, the following extinction coefficients at 280 nm were used: β-galactosidase from *E. coli*; 241590 $M^{-1}$ $cm^{-1}$, β-galactosidase from LMG P-19143; 195000 $M^{-1}$ $cm^{-1}$.

The $NH_2$-terminal amino acid sequence of the LMG P-19143 β-galactosidase was determined using a pulsed liquid phase protein sequencer (Procise Applied Biosystems 492).

SDS-polyacrylamide gel electrophoresis and isoelectric focusing were run essentially as described by the supplier of the electrophoresis equipment (Hoeffer Scientific Instruments). Isoelectric experiments were carried out using pH ranges 3.5–10 and 4–6 in 6% polyacrylamide gels containing 5.5% ampholytes. The anolyte was 0.02M acetic acid and the catholyte was 0.02M NaOH.

The activation energy ($E_a$) was determined from the slope ($-E_a/R$) of Arrhenius plot and the thermodynamic activation parameters of the reaction were calculated according to the following equations:

$$\Delta G^* = \Delta H^* - T\Delta S^* \quad \text{(Eq. 1)}$$

$$\Delta H^* = E_a - RT \quad \text{(Eq. 2)}$$

$$\Delta S^* = 2.303\, R(\log k_{cat} - 10.753 - \log T + E_a 2.303\, RT) \quad \text{(Eq. 3)}$$

The isoelectric point of the β-galactosidase from LMG P-19143 was determined at 7.8; this value is higher than that of *E. coli* β-galactosidase which was found to be 4.6 [Wallenfels K. and Weil R., 1972, In "The enzymes" (Boyer, P. D., ed) Academic Press, New York 7:617–663].

To determine the optimal pH, the enzyme activity was measured in Michaelis's barbital sodium acetate buffer with pH values from 3 to 9.5 and Sorensen's glycin II buffer with pH values from 8.5 to 13. The pH optimum for the LMG P-19143 β-galactosidase activity was found to be at pH 8.5 which is slightly higher than that of *E. coli* enzyme. Over a pH range from 6.5 to 10, both mesophilic and psychrophilic enzymes retain 90% activity after 90 minutes and 60% after 24 hours exposure. The pH stability was optimum at pH 9. The stability of LMG P-19143 β-galactosidase was also tested in various buffers 50 mM MOPS, MES, TRIS and CHES at different pH values (from 5.5 to 9.7) for 20 hours. The enzyme stability is better in MOPS buffer at pH 7.5 and in MES buffer at pH 7.

The effect of various cations such as $Zn^{2+}$, $Mn^{2+}$, $Cu^{2+}$, $Ni^{2+}$, $Li^{2+}$, $Co^{2+}$, $Ca^{2+}$, $Na^{2+}$ and $Fe^{2+}$ on the enzyme stability was also investigated. The activity of the enzyme was measured at time zero and then after 1, 2, 4 and 29 hours incubation at 4° C. The enzyme is stable in the presence of 0.1 to 1 mM $Mg^{2+}$ and also in 0.1 mM $Li^{2+}$ and 0.1 mM $Ca^{2+}$. The LMG P-19143 β-galactosidase is inhibited by $Cu^{2+}$, $Ni^{2+}$ and $Zn^{2+}$ at concentrations from 0.1 to 10 mM and by 10 mM $Fe^{2+}$.

Figure 2:
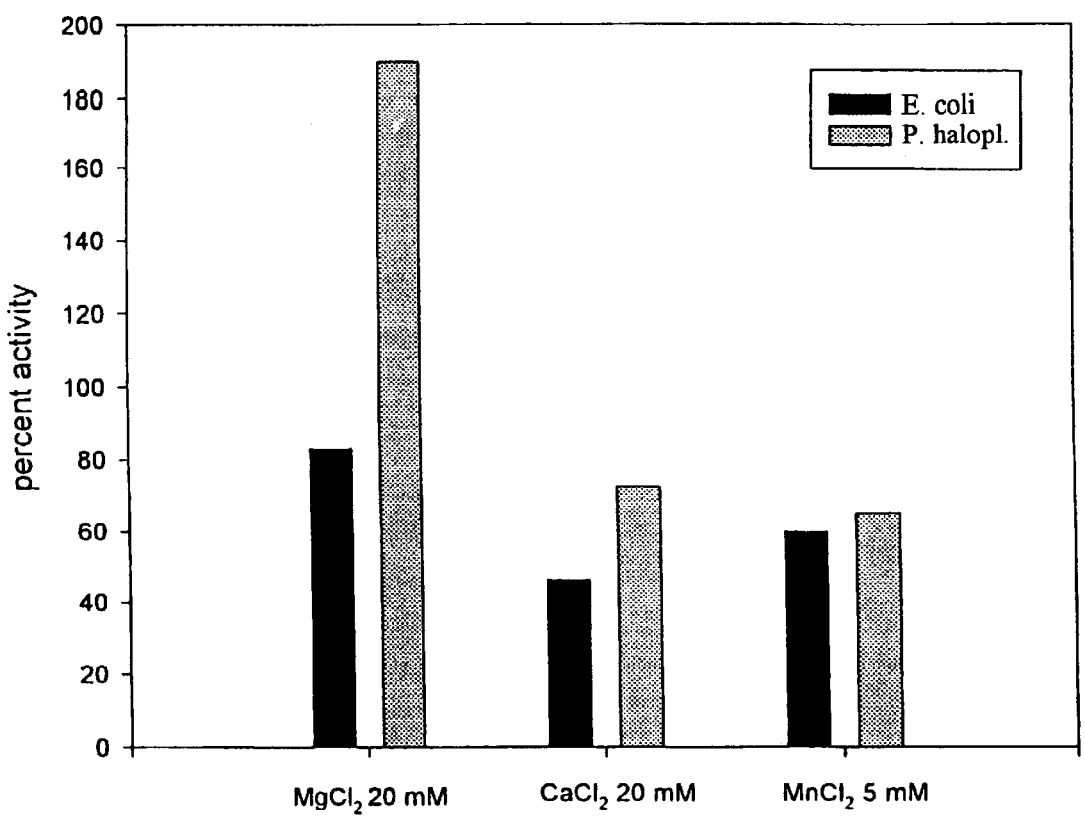
FIG. 2 shows the effects of divalent metal ions on β-galactosidase activity from *E. coli* and *Pseudoalteromonas haloplanktis* LMG P-19143.

To determine the effect of divalent metal ions on activity, assays were performed in 100 mM phosphate buffer at 25° C. and pH 7.5. The enzyme preparation was treated with 5 mM EDTA to complex metal ions. After this treatment, the enzyme showed less than 10% of its initial activity. Addition of 10 mM magnesium restored and enhanced two times the activity of LMG P-19143 β-galactosidase, 20 mM calcium or 5 mM manganese restored partially the activity of the enzyme. Addition of 20 mM $Mg^{2+}$ restored the activity of *E. coli* β-galactosidase, 20 mM $Ca^{2+}$ or $Mn^{2+}$ 5 mM restored partially the activity of *E. coli* β-galactosidase as shown in FIG. 2.

The effect of K+ was determined by assaying activity in 100 mM phosphate buffer containing KCl at concentrations from 0 to 100 mM. LMG P-19143 β-galactosidase optimal activity was recorded using a KCl concentration of 80 mM whereas the *E. coli* β-galactosidase optimal activity was recorded at a KCl concentration of 40 mM. At theses concentrations, KCl stimulated the activity of both enzymes by a factor of 1.5.

Figure 3:
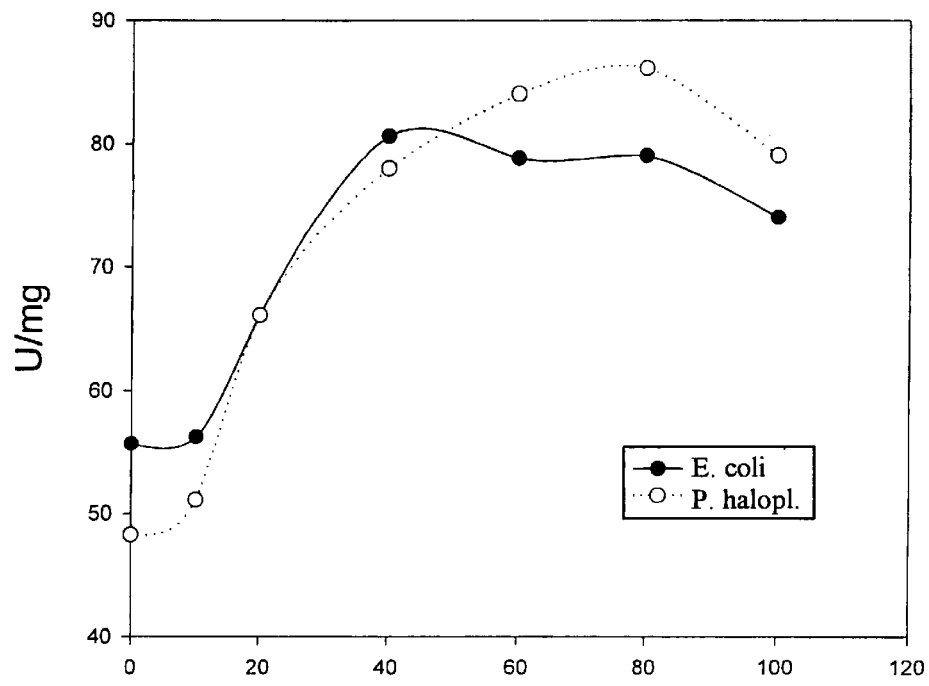
FIG. 3 shows effect of β-mercaptoethanol on kcat of β-galactosidase from *E. coli* and *Pseudoalteromonas haloplanktis* LMG P-19143 with ONPG as a substrate.

FIG. 3 shows the effect of 2-mercaptoethanol on β-galactosidase activity evaluated in the same conditions. Optimal activity of the LMG P-19143 enzyme was recorded at 80 mM 2-mercaptoethanol and that of *E. coli* enzyme at 40 mM 2-mercaptoethanol. At these concentrations, the reducing agent stimulated LMG P-19143 enzyme activity twofold and *E. coli* enzyme by a factor of 1.5.

Figure 4:
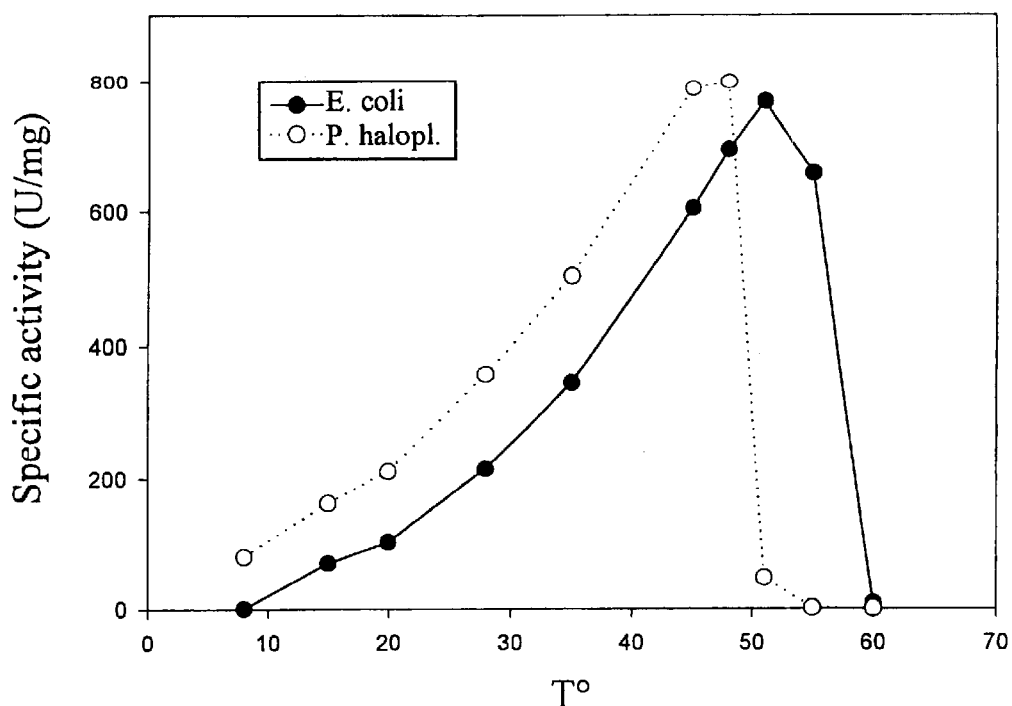
FIG. 4 shows the specific activities of β-galactosidase from *E. coli* and *Pseudoalteromonas haloplanktis* LMG P-19143, between 8 and 60° C., using ONPG as a substrate.

FIG. 4 shows the effect of temperature on the β-galactosidase activity determined by assaying the enzyme at various temperatures from 5° C. to 60° C. using ONPG as a substrate. The thermo-dependency of the activity of LMG P-19143 β-galactosidase shows a shift of the apparent optimal temperature of activity by 10° C. toward low temperatures when compared to the *E. coli* enzyme. At 8° C., the kcat ($s^{-1}$) of the LMG P-19143 enzyme is twice as high as that of *E. coli* enzyme. Theses curves have been used to construct Arrhenius plots and to calculate the activation energy parameters of the reaction as shown in table 2.

TABLE 2

Kinetic and thermodynamic activation parameters of β-galactosidase activity at 20° C. using ONPG as substrate

| Parameter | LMG P-19143 | E. coli |
|---|---|---|
| $k_{cat}$ ($s^{-1}$) | 408 | 199 |
| $E_a$ (kJ $mol^{-1}$)[a] | 15.5 | 36.2 |
| $\Delta G^*$ (kJ $mol^{-1}$) | 60.5 | 62.4 |
| $\Delta H^*$ (kJ $mol^{-1}$) | 13.1 | 33.8 |
| $\Delta S^*$ (J $mol^{-1}$ $K^{-1}$) | −162 | −97.6 |

The lower free energy of activation ($\Delta G^*$) of LMG P-19143 β-galactosidase correlates well with its higher specific activity, but the contribution of the enthalpy term ($\Delta H^*$) and of the entropy ($T\Delta S^*$) to $\Delta G^*$ also differs in both enzymes.

Figure 5:
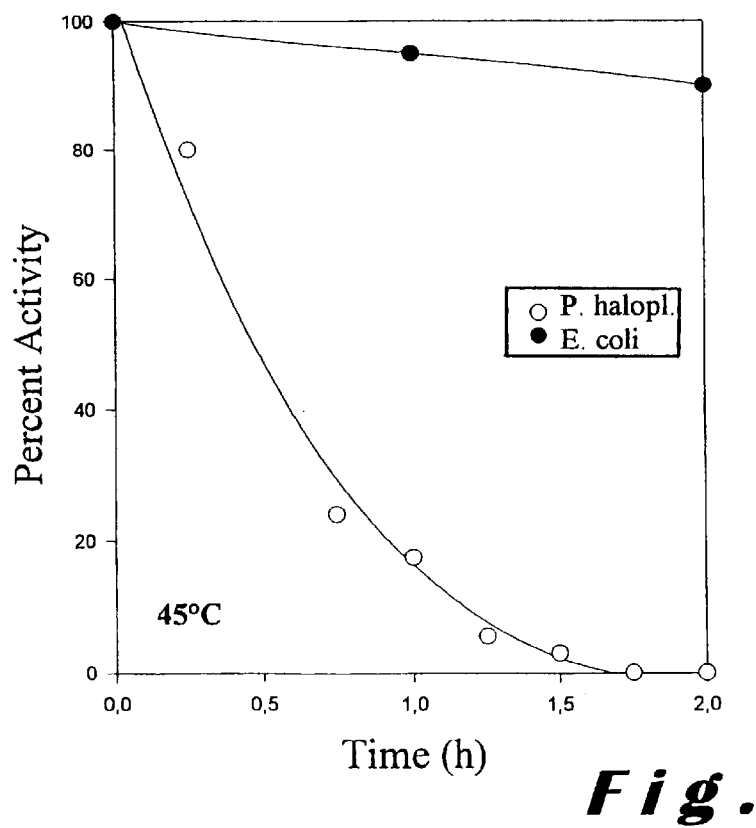
FIG. 5 shows the thermal stability of the activity of β-galacosidase from *E. coli* and from *Pseudoalteromonas haloplanktis* LMG P-19143 at 45° C., using ONPG as a substrate.

Thermal stability was determined by incubating the enzymes at different temperatures and periodically withdrawing for assay at 25° C. FIG. 5 shows that, at 45° C., the half-life of the LMG P-19143 β-galactosidase (30 min.) is 12 times lower than the half-life (6 hours) of the *E. coli* enzyme.

Figure 6:
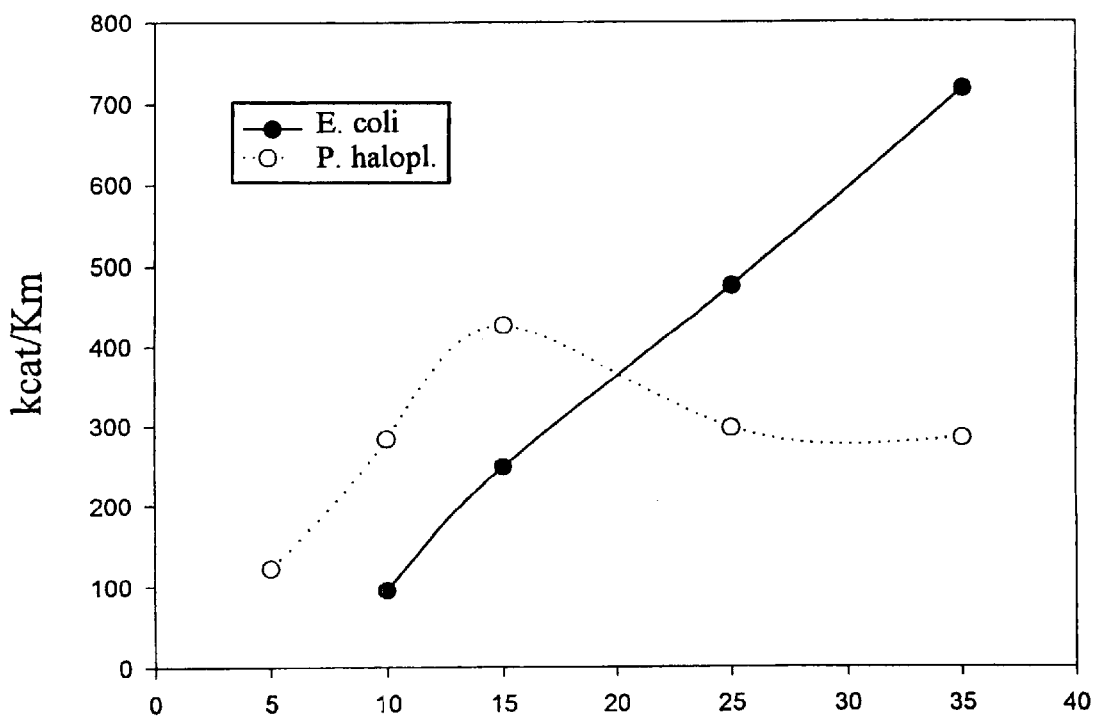
FIG. 6 shows the thermo-dependence of the physiological efficiency (kcat/km) of β-galactosidase of *Pseudoalteromonas haloplanktis* LMG P-19143, using ONPG as a substrate.

Assays were performed with ONPG as a substrate at various concentrations and at different temperatures to determine Km and $V_{max}$ values. At 10° C., the apparent Km is nearly the same for the two enzymes. Moreover, as shown in FIG. 6, the physiological efficiency (kcat/km) is about three times higher for the LMG P-19143 β-galactosidase.

Km was also determined at 25° C. with lactose (1 mM to 50 mM) as a substrate. Apparent Km was 2,4 mM with the LMG P-19143 enzyme and 13 mM with *E. coli* enzyme. LMG P-19143 β-galactosidase displays a kcat of 34, 1 U/mg and the *E. coli* enzyme a kcat of only 2, 15 U/mg. The physiological efficiency (kcat/km) of the cold-adapted enzyme is ninety times higher than that of the *E. coli* β-galactosidase.

The β-galactosidase of the present invention being purified and its physiological properties being established, a further step was to investigate the genetic characteristics of it.

DNA Isolation

DNA from strain LMG P-19143 was isolated by a modification of the method of Brahamsha, (Brahamsha B., and E. P. Greenberg, 1987, J. Bacteriol. 169:3764–3769). The lysozyme concentration was increased to 1 mg/ml and the cells were treated for 30 minutes at 37° C. The extract was then incubated in 0.5% sodium dodecyl sulphate (SDS) and proteinase K (1 μg/ml final) at 55° C. for one hour. The resulting lysate was then extracted three times with an equal volume of phenol/chloroform (50% V/V) followed by a chloroform extraction. The DNA was then precipitated with ethanol and suspended in TE buffer (10 mM Tris. Cl, 1 mM EDTA, pH 8).

Cloning

The restriction and ligation enzymes were supplied by Gibco and BMI. Genomic DNA of LMG P-19143 extracted according to the protocol described above, was digested with Sau 3Al, Hind III, Pst I or Sph I and the resulting fragments were inserted into the corresponding sites of the plasmid pSP 73 (Promega). The ligated DNA were transformed in E. coli dH5α whose endogenous β-galactosidase is inactivated by mutation. Indeed, the plasmid pSP 73 lacks a portion of the lac Z gene which provides essential α-complementation for endogeneous β-galactosidase of E. coli dH5α. The plasmid pSP 73 is directly derived from pBR 322 (Promega, USA). It displays an oligonucleotides sequence of 2464 pb (GenBank: EMBL accession number X65333). The transformants were selected on L-agar plates containing 50 μg ampicillin/ml, 0.01% X-Gal (5-bromo4-chloro-3-indolyl-α-D-galactopyranoside) and 100 μM IPTG. After two days incubation at 25° C., the β-galactosidase-positive colonies became blue. The β-galactosidase gene-containing DNA fragment was subcloned into the polylinker of pSP 73 by digestion with Xba I, Bgl II or Eco RI and plasmid self ligation. The sub-clones were analysed by testing β-galactosidase activity on L-agar plates containing 50 μg ampicillin/ml, 0.01% X-gal and 100 μM IPTG.

For DNA sequencing, the sub-clone Eco RI was ligated in pK 19 (Pridmore R. D., 1987, Gene 56:309–312). DNA sequencing was performed using the chromosome walking technique with 5' Fluorescein labelled primers. The products of the sequencing reaction were analysed on ALF DNA sequencer (Pharmacia, Sweden). Synthetic oligonucleotides used as primers were from Eurogentec S. A.

The N-terminal amino sequence of the purified enzyme according to the present invention has been determined and alignment of the first nineteen amino acids of LMG P-19143 β-galactosidase with the N-terminal sequence of the E. coli enzyme showed ten conserved positions.

Cloning of the LMG P-19143 β-galactosidase Gene

Four genomic libraries of LMG P-19143 DNA were constructed by restriction digestion of DNA with Sau 3AI, Hind III, Pst I or Sph I and ligation into the corresponding sites of the vector pSP 73.

pSP 73 plasmid lacks the lac Zα fragment which could complement the E. coli dH5α deleted β-galactosidase. Transformants of E. coli dH5α containing the pSP 73 vector without any insert produced white colonies on X-gal plates. From the colonies screened at 25° C., three β-galactosidase positive colonies were obtained. The DNA inserts of these three β-galactosidase positive transformants were the same and this insert is a fragment Pst I-Pst I of nearly 9 kb.

A restriction map of clone Pst I-Pst I was generated and fragments were subcloned to determine the smallest fragment which could encode the β-galactosidase gene. The colonies obtained were analysed on the basis of β-galactosidase activity on X-gal plates. Three clones which produced β-galactosidase activity were found; theses clones were the result of restriction digestion Xba I, BgI II and Eco RI. The Eco RI fragment was chosen for sequencing.

Nucleotide Sequence of the LMG P-19143 β-galactosidase Gene

The Eco-RI-Pst I fragment of 5088 bp has been totally sequenced. A single large open reading frame was found starting with an ATG at nucleotide 1531 and ending with a TAG at nucleotide 4649; it has been sequenced four times on both strands and its sequence is shown in SEQ ID NO1. The first $NH_2$ terminal amino acids of the native protein determined by EDMAN degradation could be recognised following the ATG of the open reading frame. Therefore the protein corresponds to 1038 amino acids with a calculated $M_r$ of 118068. The predicted amino acid sequence of the sequenced gene was compared with protein sequences databases with "BLAST network service" program. The protein sequence shown in SEQ ID NO2 was aligned with E. coli lac Z gene by "TFASTA" program with 51% sequence similarities. The LMG P-19143 gene was so designated lac Z on the basis of its sequence similarities with the lac Z from E. coli. The alignment showed that the proposed active-site residues in E. coli lac Z; Glu-461, Glu-537, Met 502 and Tyr 503 are conserved in the LMG P-19143 sequence. The alignment with other lac Z β-galactosidase showed significant homology surrounding Glu-461 and Glu-537, forming consensus sequences. The tyrosine residue which is important for the reaction is also conserved in the LMG P-19143 sequence.

The β-galactosidase protein sequence analysis had allowed to identify structural features typical of cold-adapted enzymes. For the LMG P-19143 protein, Arginine content (39) and Arg/Arg+Lys ratio (0.47) are smaller than for E. coli β-galactosidase, 66 and 0.77, respectively. The proline residues content is also smaller for the cold-adapted enzyme (46 and 62 respectively) and its glycine content was higher within the 15 amino acids around the catalytic residue Glu 461.

Alignment with E. coli lac Z gene showed three insertions in the LMP-19143 lac Z gene. These insertions of 4, 5 and 9 residues are located at Glu 78, Gln 634 and Asn 739 respectively.

The LMG P-19143 β-galactosidase shares structural properties with the mesophilic E. coli β-galactosidase. The apparent sub-unit mass of the LMG P-19143 β-galactosidase is comparable to that of E. coli enzyme. The cold-adapted enzyme is a multimer since it is concentrated by an ultra-filtration membrane of 300 kDa cut off. The sub-unit is long of 1038 amino acids with a Mr of 118,068, which is slightly higher than that of E. coli lac Z enzyme with 1,023 amino acids.

The β-galactosidase from LMG P-19143 shows an optimal pH value of 8.5 for both stability and activity which is comparable to what is observed for the E. coli β-galactosidase. The two enzymes have a good activity within the pH range of 6.6–10, this would allow the efficient treatment of milk, the pH of which is 6.6.

LMG P-19143 and E. coli β-galactosidase are activated by 2-mercaptoethanol. SH-groups may be involved in the catalytic process but other data show that certain SH-groups may be important for maintaining the active conformation of the enzyme [Wallenfels K. and Weil R., 1972. In "The enzymes" (Boyer, P. D., ed.) Academic Press, New York 7:617–663].

As many fungal and bacterial β-galactosidase, LMG P-19143 and E. coli enzymes require divalent cations for activity. Indeed, addition of EDTA, a chelating agent, to the assay mixture leads to enzyme inactivation. Addition of magnesium, calcium or manganese restored the activity. So LMG P-19143 β-galactosidase is a metallo-enzyme having a strict requirement for divalent metal ions as suggested for *E. coli* β-galactosidase by Wallenfels K. and Weil R. in "The enzymes" (Boyer, P. D., ed., Academic Press, New York 7:617–663, 1972). Moreover the three-dimensional structure of *E. coli* β-galactosidase showed two bound magnesium per monomer (Jacobson R. H., Zhang X-J., DuBose R. F. and Matthews B. W., 1994. Nature 369:761–766).

The alignment of LMG P-19143 sequence with other lac Z β-galactosidase showed the conservation of the amino acid residues involved in catalysis. The proposed mechanism of action for the *E. coli* lac Z β-galactosidase involves a double displacement reaction in which the enzyme forms and hydrolyses a glycosyl-enzyme intermediate via oxocarbonium ion-like transition states (Gebler, J. C., R. Aebersold, and S. G. Withers, 1992. J. Biol. Chem. 267:11126–11130). These authors identified Glu-537 as the nucleophilic amino acid and suggested that Glu-461 serves as the general acid/base catalyst which protonates the galactosyl transition state intermediate and deprotonates the attaching water in the *E. coli* lac Z protein. The analysis of the three-dimensional structure of β-galactosidase from *E. coli* showed that residues Glu 461, Met 502, Tyr 503 and Glu 537 are found closed together and formed a pocket that was identified as the substrate binding site. Glu 537 is situated on the opposite site of the cavity and oriented through hydrogen bonding with Tyr 503 and Arg 388 (Jacobson R. H., Zhang X-J., DuBose R. F. and Matthews B. W., 1994. Nature 369:761–766). These residues are also conserved in the LMG P-19143 sequence. Affinity labelling of β-galactosidase has identified Met-502 as a non-essential active site residue, whereas the suggestion that the adjacent residue, Tyr-503, may play a direct role as an acid/base catalyst, was supported by subsequent analysis of mutants modified at this position (Gebler, J. C., R. Aebersold, and S. G. Withers, 1992. J. Biol. Chem. 267:11126–11130). Among homologous β-galactosidase sequences, residues that form the active-site pocket are highly conserved (Jacobson R. H., Zhang X-J., DuBose R. F. and Matthews B. W., 1994. Nature 369:761–766).

LMG P-19143 β-galactosidase also shares common properties with cold-adapted enzymes (Feller G., Arpigny J. L., Narinx E., and Gerday C., 1997. Comp. Biochem. Physiol. 118A:495–499).

Indeed the cold β-galactosidase displays a lower apparent optimum temperature of activity and a lower thermal stability than the *E. coli* enzyme. Moreover over the temperature range of 0–40° C., the lever of turnover (kcat) of LMG P-19143 β-galactosidase towards ONPG is higher than that *E. coli* enzyme. This difference in favour of the cold-adapted enzyme is dramatically increased when lactose is used as substrate (fifteen times at 25° C.). The thermodynamic parameters showed in (Table 2) are consistent with the fact that the activated state of the complex is reached through a minimum of entropy change and with a lower activation enthalpy when compared to *E. coli* β-galactosidase.

With ONPG as a substrate, the km values are, at low temperature, comparable for both enzymes. However, since kcat value is significantly higher to LMG P-19143 β-galactosidase, the physiological efficiency is also higher for the LMG P-19143 β-galactosidase.

With lactose as a substrate at 25° C., km is five times lower for the LMG P-19143 enzyme and the physiological efficiency (kcat/Km) is therefore eighty times as high as that of *E. coli* β-galactosidase.

The above mentioned data allow to clarify to some extent some questions raised about the possible differences in the molecular adaptation of intracellular enzymes when compared to extracellular ones (Gerday et al., 1998). Indeed in a few cases: citrate synthase and β-galactosidase, the specific activity was not higher than the mesophilic counterparts whereas thermostability was, in all cases, much lower than that of mesophilic enzymes.

The alignment of the amino acid sequence of LMG P-19143 β-galactosidase with that of *E. coli* β-galactosidase shows three insertions of 4, 5 and 9 residues. If located in surface loops, these insertions could contribute to increase the plasticity of the molecular edifice as also suggested in the case of subtilisin S41 (Davail S., Feller G., Narinx E. and Gerday C., 1994, J. Biol. Chem. 269:17448–17453). Nevertheless the involvement of indels in cold-adaptation is strongly specific to each enzyme type and can not be generalised (Feller G., Arpigny J. L., Narinx E., and Gerday C., 1997. Comp. Biochem. Physiol. 118A:495–499).

As in the case of several cold-adapted enzymes, the LMG P-19143 β-galactosidase arginine content (55) is lower than that of its mesophilic counterpart (66). Arginine residues play a significant role in thermal adaptation. Indeed, the charge resonance of the guanidium group gives arginine the possibility to form more than one salt bridge (Mrabet et al., 1992) as well as multiple hydrogen bonds with surrounding acceptors (Borders, CL. L, Broadwater, J. A.; Bekeny, P. A., Salmon, J. A., Lee, A. S., Eldrige, A. M., Pett, V. B., 1994, Protein Sci. 3:541–548). The multivalent character of arginine certainly account for its low occurrence in many cold-adapted enzymes and in enzymes of low stability in general (Menendez-Ariaz, M. and Argos, P, 1989, J. Mol. Biol. 206:397–406).

The cold-adapted enzyme also shows a lower content of proline (46 compared to 62 in the mesophilic enzyme). The cyclic structure of proline severely impairs the rotations about its N—$C^{\alpha}$ bond. So, the presence of this residue in a protein greatly reduces the number of possible local conformations of the molecular backbone. This reduces the conformational entropy of the unfolded state and confers more rigidity to the native protein (Matthews et al., 1987).

On the contrary, LMG P-19143 β-galactosidase glycine content is lower than that *E. coli* enzyme. Glycine, which has a side chain, increases the degrees of freedom of the unfolded polypeptide backbone. The replacement of one Gly by another residue in theory can reduce the backbone flexibility and destabilises the unfolded state by as much as 3,3 kJ mol$^{-1}$ at 65° C. (Nemethy et al., 1966). Nevertheless it has been suggested that the stacking of Gly around the catalytic residues provides high active site flexibility (Karplus and Shultz, 1985).

To conclude, LMG P-19143 β-galactosidase is a cold-adapted enzyme that is much more active at low and moderate temperatures when compared to the mesophilic enzyme from *E. coli*. Moreover the ideal optimum pH range (6–8) is suitable for lactose hydrolysis in milk and dairy products.

What is claimed is:

1. A purified cold-active beta galactosidase enzyme, specific for lactose, having a stable enzymatic activity at a temperature below 8° C. and being produced by the psychrophilic bacterium *Pseudoalteromonas haloplanktis*.

2. The purified cold-active beta galactosidase enzyme according to claim 1, having a stable enzymatic activity at a temperature ranging from 0° C. up to but below 8° C.

3. The purified cold-active beta galactosidase enzyme according to claim 1, having a stable enzymatic activity at a pH ranging from 6 to 10.

4. The purfied cold-active beta galactosidase enzyme according to claim 1, having a stable enzymatic activity in the presence of at least one substance selected from the group consisting of calcium and galactose.

5. The purified cold-active beta galactosidase enzyme according to claim 1, characterized by being inactivated at pasteurization temperatures.

6. The purified cold-active beta galactosidase enzyme according to claim 1, characterized in that it is produced by the psychrophilic bacterium *Pseudoalteromonas haloplanktis* given the BCCM™ Accession Number LMG P-19143.

7. The purified cold-active beta galactosidase enzyme according to claim 1, having a stable enzymatic activity at a refrigerating conservation temperature for dairy products.

8. The purified cold-active beta galactosidase enzyme according to claim 7, being inactivated at pasteurization temperatures.

9. The purified cold-active beta galactosidase enzyme according to claim 7, having a stable enzymatic activity at a pH ranging from 6 to 10.

10. The purified cold-active beta galactosidase enzyme according to claim 7, having a stable enzymatic activity in the presence of at least one substance selected from the group consisting of calcium and galactose.

11. The purified cold-active beta galactosidase enzyme according to claim 7, having a stable enzymatic activity at a temperature lower than 6° C.

12. The purified cold-active beta galactosidase enzyme according to claim 7, having a stable enzymatic activity at a temperature of 4° C.

13. The purified cold-active beta galactosidase enzyme according to claim 6, having a stable enzymatic activity at a temperature lower than 6° C.

14. The purified cold-active beta galactosidase enzyme according to claim 6, having a stable enzymatic activity at a temperature of 4° C.

15. The purified cold-active beta galactosidase enzyme according to claim 6, being inactivated at pasteurization temperatures.

16. The purified cold-active beta galactosidase enzyme according to claim 6, having a stable enzymatic activity at a pH ranging from 6 to 10.

17. The purified cold-active beta galactosidase enzyme according to claim 6, having a stable enzymatic activity in the presence of at least one substance selected from the group consisting of calcium and galactose.

18. The purified cold-active beta galactosidase enzyme according to claim 6, having a stable enzymatic activity at a refrigerating conservation temperature for dairy products.

19. A purified cold-active beta galactosidase enzyme, having stable enzymatic activity between 0° C. and 50° C., in the presence of lactose, said enzyme being produced by the psychrophilic bacterium *Pseudoalteromonas haloplanktis* given the BCCM™ Accession Number LMG P-19143.

20. A purified cold-active beta galactosidase enzyme, having stable enzymatic activity between 0° C. and 50° C., in the presence of lactose, said enzyme being produced by the psychrophilic bacterium *Pseudoalteromonas haloplanktis* given the BCCM™ Accession Number LMG P-19143, and having a stable enzymatic activity in the presence of at least one substance selected from the group consisting of calcium and galactose.

21. A method for producing a cold-active beta galactosidase enzyme according to claim 1, comprising the steps of:
   extracting nucleic acids from *Pseudoalteromonas haloplanktis*,
   constructing a recombinant expression vector comprising a nucleic acid which encodes said cold-active beta galactosidase enzyme,
   transforming a host cell with at least one such said recombinant expression vector,
   culturing said transformed host, and
   recovering the produced polypeptide having the biological activity of said cold-active beta galactosidase enzyme.

22. A method for reducing lactose content in dairy products, comprising the step of:
   contacting the dairy product with a purified cold-active beta galactosidase enzyme according to claim 1, at a refrigeration temperature and at a pH ranging from 6–10.

23. The method according to claim 22, further comprising the step of heating said contacted dairy product at a pasteurization temperature sufficient to denature said cold-active beta galactosidase enzyme.

24. The purified cold-active beta galactosidase enzyme according to claim 1, which is efficacious for hydrolyzing lactose in milk or dairy products at a temperature below 8° C.

* * * * *

SEQUENCE LISTING

<160> NUMBER OF SEQ ID NOS: 2

<210> SEQ ID NO 1
<211> LENGTH: 3171
<212> TYPE: DNA
<213> ORGANISM: Pseudoalteromonas haloplanktis

<400> SEQUENCE: 1

```
tagctatatt tagcgccatt ataattgccc gtttatgcaa caggaataaa catgacctct      60
ttacagcaca taattaatcg tcgcgattgg gaaaatccaa ttacagtaca agttaatcaa     120
gtaaaagcac atagcccact taacggcttt aaaacaattg aagacgcccg tgaaaataca     180
cagtcgcaga agaaaagttt aaacgggcag tgggatttta aattatttga taagcccgaa     240
gcggtcgatg agtcgttatt gtatgagaag ataagtaaag agctaagcgg cgactggcaa     300
agtattactg tgccttctaa ctggcaacta cacggctttg ataaacccat ttactgtaat     360
gttaaatacc catttgcagt aaacccgcca tttgtaccaa gcgataaccc tactggttgt     420
taccgcactg aatttacaat cacacctgag cagttaacgc agcgtaacca tataattttt     480
gaaggcgtta actcggcttt tcatctttgg tgtaacgggc agtgggtggg gtattcacaa     540
gatagccgct taccgagcga atttgattta agtgagcttt tagttgtcgg tactaaccgt     600
attgccgtta tggttattcg ttggagtgat ggcagttatt tagaagatca ggatatgtgg     660
tggctaagcg gtattttcg cgatgttaac ttacttacaa aaccgcaaag ccaaatacgc     720
gatgtgttta taaccccga tttagacgct tgctatcgcg atgcaacgct acatataaaa     780
actgcgataa atgcgccaaa taactaccaa gtagcagtac agatttttga tggtaaaaca     840
tcactgtgcg agccgaaaat tcaaagcact aacaataaac gtgttgatga aaaggggggg     900
tggagcgatg tcgtatttca aacaatagca atacgaagcc ctaaaaagtg gaccgccgaa     960
acgccgtact tatatcgttg cgtagtaagc ctgcttgatg aacaaggcaa tacagtcgac    1020
gttgaagcct ataacattgg ttttagaaaa gtagaaatgc ttaacgggca gctgtgtgta    1080
aatggcaaac cgttacttat acgggtgtt aaccgacacg aacatcaccc agaaaacggc    1140
catgctgtta gcactgccga tatgattgaa gatattaagc tgatgaagca aaataacttt    1200
aatgccgtac gtacagctca ttaccctaac catccacttt tttacgagct atgtgacgag    1260 ctaggttat acgtggttga tgaagcgaat atagaaaccc atggcatgtt tcctatgggg    1320
cgtttagcaa gcgatccgct atgggcaggt gcatttatgt cgcgttatac gcaaatggtt    1380
gagcgcgata aaaaccacgc ctcaattatt atttggtcac ttggaaacga atgcgggcac    1440
ggcgcaaatc atgatgctat gtatggctgg tcaaaaagct ttgacccttc tcgcccagtg    1500
caatacgagg gcggcggtgc aaacacgaca gctaccgata ttatttgccc aatgtactcc    1560
cgtgtagata ccgatattaa agacgatgcg gtacctaagt attcaattaa aaaatggctg    1620
agcttaccgg gtgaaactcg tccacttatt ttatgtgagt acgccatgc tatgggtaat    1680 agcttaggta gctttgacga ttactggcag gcatttagag aatacccacg gctgcaaggc    1740
ggctttattt gggattggt agatcaaggt ttatctaaaa ttgacgagaa cggcaagcat    1800
tattgggctt acggcggcga ctttggtgat gaactaaacg accgccagtt ttgtataaac    1860
ggcttattgt tcccggatcg tacaccgcat cctagcctat ttgaagctaa atacagccag    1920
caacatttac aatttacact gcgcgagcaa aatcaaaatc aaaaccaaaa ccaatacagc    1980
attgatgtat ttagcgatta cgtatttagg cacaccgata acgaaaaact cgtttggcaa    2040
```

-continued

```
ttaatacaaa atggcgtgtg tgttgagcaa ggcgaaatgg cacttaatat tgctccgcaa    2100
agtacgcaca ctttaaccat taaaactaaa acagcgtttg agcatggtgc gcaatattac    2160
cttaatttag atgtagcact aattaacgac tcacactttg caaacgctaa tcacgttatg    2220
gattcagaac agtttaagct tataaatagt aataatttaa acagtaaatc atttgcatca    2280
gctacagaga aaagcgttat aagtgttaat gaaaccgact cccacctaag tattgaaaac    2340
aatacattta aacttgtttt taatcaacaa tcaggactta tagagcagtg gttacaagac    2400
gatacacagg ttattagtag cccactggtt gataactttt atcgtgcccc acttgataac    2460
gacattggtg taagcgaagt ggacaaccta gaccctaatg catgggaagc acgctggtcg    2520
cgcgcaggta tagggcaatg gcagcgcaca tgtagctcaa tcaatgctgt gcaatcaagc    2580
gttgatgtcc gtattacttg tgtatttaat tacgaattta atggcgtgct acaagcacaa    2640
acacagtggc tatatacgct caataataca ggtactatta gcttaaatgt tgatgtgaac    2700
ttaaacgaca ccctaccacc aatgccgcga atagggttaa gtacaacgat taacaagcaa    2760
agcgatacaa aagtaaactg gctagggtta ggtccttttg aaaactaccc agatcgtaaa    2820
tccgctgcac gttttggtta ttacagcttg agcttaaatg agctatatac accgtatata    2880
ttcccaactg ataacggtct gcgtagcgat tgccaattac tgagcattaa taacttaatc    2940
gtgactggcg cgttttttgtt tgccgccagt gagtattcgc aaaatatgct aacgcaagct    3000
aaacacacta acgaactaat tgctgatgat tgcattcatg tacatattga tcatcaacat    3060
atgggtgtag gtgcgatga ttcgtggagt ccaagtaccc ataaagagta tttattagag    3120
caaaaaaatt ataattactc gcttacactt actggggga ttacaactta a            3171
```

<210> SEQ ID NO 2
<211> LENGTH: 1039
<212> TYPE: PRT
<213> ORGANISM: Pseudoalteromonas haloplanktis
<220> FEATURE:
<221> NAME/KEY: ACT_SITE
<222> LOCATION: (460)
<221> NAME/KEY: ACT_SITE
<222> LOCATION: (501)
<221> NAME/KEY: ACT_SITE
<222> LOCATION: (502)
<221> NAME/KEY: ACT_SITE
<222> LOCATION: (536)
<221> NAME/KEY: SIMILAR
<222> LOCATION: (533)..(543)
<221> NAME/KEY: SIMILAR
<222> LOCATION: (455)..(460)

<400> SEQUENCE: 2

```
Met Thr Ser Leu Gln His Ile Ile Asn Arg Arg Asp Trp Glu Asn Pro
  1               5                  10                  15

Ile Thr Val Gln Val Asn Gln Val Lys Ala His Ser Pro Leu Asn Gly
             20                  25                  30

Phe Lys Thr Ile Glu Asp Ala Arg Glu Asn Thr Gln Ser Gln Lys Lys
         35                  40                  45

Ser Leu Asn Gly Gln Trp Asp Phe Lys Leu Phe Asp Lys Pro Glu Ala
     50                  55                  60

Val Asp Glu Ser Leu Leu Tyr Glu Lys Ile Ser Lys Glu Leu Ser Gly
 65                  70                  75                  80

Asp Trp Gln Ser Ile Thr Val Pro Ser Asn Trp Gln Leu His Gly Phe
                 85                  90                  95

Asp Lys Pro Ile Tyr Cys Asn Val Lys Tyr Pro Phe Ala Val Asn Pro
```

-continued

```
                    100                 105                 110
Pro Phe Val Pro Ser Asp Asn Pro Thr Gly Cys Tyr Arg Thr Glu Phe
            115                 120                 125
Thr Ile Thr Pro Glu Gln Leu Thr Gln Arg Asn His Ile Ile Phe Glu
        130                 135                 140
Gly Val Asn Ser Ala Phe His Leu Trp Cys Asn Gly Gln Trp Val Gly
145                 150                 155                 160
Tyr Ser Gln Asp Ser Arg Leu Pro Ser Glu Phe Asp Leu Ser Glu Leu
                165                 170                 175
Leu Val Val Gly Thr Asn Arg Ile Ala Val Met Val Ile Arg Trp Ser
            180                 185                 190
Asp Gly Ser Tyr Leu Glu Asp Gln Asp Met Trp Trp Leu Ser Gly Ile
        195                 200                 205
Phe Arg Asp Val Asn Leu Leu Thr Lys Pro Gln Ser Gln Ile Arg Asp
    210                 215                 220
Val Phe Ile Thr Pro Asp Leu Asp Ala Cys Tyr Arg Asp Ala Thr Leu
225                 230                 235                 240
His Ile Lys Thr Ala Ile Asn Ala Pro Asn Asn Tyr Gln Val Ala Val
                245                 250                 255
Gln Ile Phe Asp Gly Lys Thr Ser Leu Cys Glu Pro Lys Ile Gln Ser
            260                 265                 270
Thr Asn Asn Lys Arg Val Asp Glu Lys Gly Gly Trp Ser Asp Val Val
        275                 280                 285
Phe Gln Thr Ile Ala Ile Arg Ser Pro Lys Lys Trp Thr Ala Glu Thr
    290                 295                 300
Pro Tyr Leu Tyr Arg Cys Val Ser Leu Leu Asp Glu Gln Gly Asn
305                 310                 315                 320
Thr Val Asp Val Glu Ala Tyr Asn Ile Gly Phe Arg Lys Val Glu Met
                325                 330                 335
Leu Asn Gly Gln Leu Cys Val Asn Gly Lys Pro Leu Leu Ile Arg Gly
            340                 345                 350
Val Asn Arg His Glu His His Pro Glu Asn Gly His Ala Val Ser Thr
        355                 360                 365
Ala Asp Met Ile Glu Asp Ile Lys Leu Met Lys Gln Asn Asn Phe Asn
    370                 375                 380
Ala Val Arg Thr Ala His Tyr Pro Asn His Pro Leu Phe Tyr Glu Leu
385                 390                 395                 400
Cys Asp Glu Leu Gly Leu Tyr Val Val Asp Glu Ala Asn Ile Glu Thr
                405                 410                 415
His Gly Met Phe Pro Met Gly Arg Leu Ala Ser Asp Pro Leu Trp Ala
            420                 425                 430
Gly Ala Phe Met Ser Arg Tyr Thr Gln Met Val Glu Arg Asp Lys Asn
        435                 440                 445
His Ala Ser Ile Ile Trp Ser Leu Gly Asn Glu Cys Gly His Gly
    450                 455                 460
Ala Asn His Asp Ala Met Tyr Gly Trp Ser Lys Ser Phe Asp Pro Ser
465                 470                 475                 480
Arg Pro Val Gln Tyr Glu Gly Gly Ala Asn Thr Thr Ala Thr Asp
                485                 490                 495
Ile Ile Cys Pro Met Tyr Ser Arg Val Asp Thr Asp Ile Lys Asp Asp
            500                 505                 510
Ala Val Pro Lys Tyr Ser Ile Lys Lys Trp Leu Ser Leu Pro Gly Glu
        515                 520                 525
```

-continued

```
Thr Arg Pro Leu Ile Leu Cys Glu Tyr Ala His Ala Met Gly Asn Ser
    530                 535                 540
Leu Gly Ser Phe Asp Asp Tyr Trp Gln Ala Phe Arg Glu Tyr Pro Arg
545                 550                 555                 560
Leu Gln Gly Gly Phe Ile Trp Asp Trp Val Asp Gln Gly Leu Ser Lys
                565                 570                 575
Ile Asp Glu Asn Gly Lys His Tyr Trp Ala Tyr Gly Gly Asp Phe Gly
                580                 585                 590
Asp Glu Leu Asn Asp Arg Gln Phe Cys Ile Asn Gly Leu Leu Phe Pro
            595                 600                 605
Asp Arg Thr Pro His Pro Ser Leu Phe Glu Ala Lys Tyr Ser Gln Gln
            610                 615                 620
His Leu Gln Phe Thr Leu Arg Glu Gln Asn Gln Asn Gln Asn Gln Asn
625                 630                 635                 640
Gln Tyr Ser Ile Asp Val Phe Ser Asp Tyr Val Phe Arg His Thr Asp
                645                 650                 655
Asn Glu Lys Leu Val Trp Gln Leu Ile Gln Asn Gly Val Cys Val Glu
                660                 665                 670
Gln Gly Glu Met Ala Leu Asn Ile Ala Pro Gln Ser Thr His Thr Leu
            675                 680                 685
Thr Ile Lys Thr Lys Thr Ala Phe Glu His Gly Ala Gln Tyr Tyr Leu
            690                 695                 700
Asn Leu Asp Val Ala Leu Ile Asn Asp Ser His Phe Ala Asn Ala Asn
705                 710                 715                 720
His Val Met Asp Ser Glu Gln Phe Lys Leu Ile Asn Ser Asn Asn Leu
                725                 730                 735
Asn Ser Lys Ser Phe Ala Ser Ala Thr Glu Lys Ser Val Ile Ser Val
                740                 745                 750
Asn Glu Thr Asp Ser His Leu Ser Ile Glu Asn Asn Thr Phe Lys Leu
            755                 760                 765
Val Phe Asn Gln Gln Ser Gly Leu Ile Glu Gln Trp Leu Gln Asp Asp
            770                 775                 780
Thr Gln Val Ile Ser Ser Pro Leu Val Asp Asn Phe Tyr Arg Ala Pro
785                 790                 795                 800
Leu Asp Asn Asp Ile Gly Val Ser Glu Val Asp Asn Leu Asp Pro Asn
                805                 810                 815
Ala Trp Glu Ala Arg Trp Ser Arg Ala Gly Ile Gly Gln Trp Gln Arg
            820                 825                 830
Thr Cys Ser Ser Ile Asn Ala Val Gln Ser Ser Val Asp Val Arg Ile
            835                 840                 845
Thr Cys Val Phe Asn Tyr Glu Phe Asn Gly Val Leu Gln Ala Gln Thr
850                 855                 860
Gln Trp Leu Tyr Thr Leu Asn Asn Thr Gly Thr Ile Ser Leu Asn Val
865                 870                 875                 880
Asp Val Asn Leu Asn Asp Thr Leu Pro Pro Met Pro Arg Ile Gly Leu
                885                 890                 895
Ser Thr Thr Ile Asn Lys Gln Ser Asp Thr Lys Val Asn Trp Leu Gly
                900                 905                 910
Leu Gly Pro Phe Glu Asn Tyr Pro Asp Arg Lys Ser Ala Ala Arg Phe
            915                 920                 925
Gly Tyr Tyr Ser Leu Ser Leu Asn Glu Leu Tyr Thr Pro Tyr Ile Phe
930                 935                 940
```

-continued

```
Pro Thr Asp Asn Gly Leu Arg Ser Asp Cys Gln Leu Leu Ser Ile Asn
945             950             955             960

Asn Leu Ile Val Thr Gly Ala Phe Leu Phe Ala Ala Ser Glu Tyr Ser
            965             970             975

Gln Asn Met Leu Thr Gln Ala Lys His Thr Asn Glu Leu Ile Ala Asp
        980             985             990

Asp Cys Ile His Val His Ile Asp His Gln His Met Gly Val Gly Gly
    995             1000            1005

Asp Asp Ser Trp Ser Pro Ser Thr His Lys Glu Tyr Leu Leu Glu Gln
    1010            1015            1020

Lys Asn Tyr Asn Tyr Ser Leu Thr Leu Thr Gly Gly Ile Thr Thr
1025            1030            1035
```